US00PP14018P29

(12) United States Plant Patent
Drewlow

(10) Patent No.: US PP14,018 P2
(45) Date of Patent: Jul. 29, 2003

(54) POINSETTIA PLANT NAMED 'FESTIVAL ROSE'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/447,596

(22) Filed: Nov. 23, 1999

(51) Int. Cl.[7] ..... A01H 5/00

(52) U.S. Cl. ..... Plt./307

(58) Field of Search ..... Plt./307

*Primary Examiner*—Bruce R. Campell
*Assistant Examiner*—Michelle Kizilkaya
(74) *Attorney, Agent, or Firm*—Webb Ziesenheim Logsdon Orkin & Hanson, P.C.

(57) ABSTRACT

A poinsettia plant named 'Festival Rose' particularly characterized by the characteristics of unique rose color in habit and bract. The plant is resistant to bract fading and is a long lasting cultivar. The plant has strong branch angles which reduce breakage of lateral branches during shipping.

1 Drawing Sheet

BACKGROUND OF THE NEW PLANT

The present invention comprises a new and distinct cultivar of *Euphorbia pulcherrima* known by the varietal name 'Festival Rose'.

The new cultivar was discovered in a planned breeding program and is a controlled cross of Breeding Stock No. 93-556-1 (seed parent), unpatented×'Lilo Pink' (pollen parent), U.S. Plant Pat. No. 7,716. It was then grafted to Stock Plant No. 94-G-143 to make a branching type plant from the original non-branching seedling in 1994 at Lompoc, Calif.; was first asexually reproduced by cuttings thereafter in Lompoc, Calif. and has been repeatedly asexually reproduced by cuttings at Lompoc, Calif. Continued observations from the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Unique rose color in habit and bract shape.

2. Resistant to bract fading as plant ages and under low light levels of home conditions.

3. Long lasting cultivar.

4. Strong branch angles reduce breakage of lateral branches during shipping.

The following characteristics distinguish the new Poinsettia from other cultivated Poinsettias of this type known to the inventor. The characteristics are described with comparative reference to the cultivar 'Freedom Rose' (unpatented).

1. 'Festival Rose' has a similar bract color to 'Freedom Rose' of Red Group 53C and a similar bract diameter of 25 to 30 cm.

2. 'Festival Rose' has a plant height of 30 to 33 cm while 'Freedom Rose' has a plant height of 27 to 30 cm.

3. 'Festival Rose' has a plant spread of 45 to 50 cm while 'Freedom Rose' has a plant height of 40 to 45 cm.

4. 'Festival Rose' has strong branch angles which results in about 9% breakage in shipping tests while 'Freedom Rose' has moderate branch angles which results in about 31.5% breakage in shipping tests.

DESCRIPTION OF THE DRAWING

The accompanying photographic drawing illustrates the new cultivar, the color being as nearly true as possible with color illustrations of this type. The photograph was taken under studio conditions seventeen weeks after rooted cuttings were planted in Lompoc, Calif.

DESCRIPTION OF THE NEW PLANT

The following detailed description sets forth the characteristics of the new cultivar. The data which defines these characteristics were collected from asexual reproductions carried out in Lompoc, Calif. The description of the plant is based on observations of a new plant propagated from the grafted plant with self-branching agent transferred. The plant history was taken on a plant grown in a 15 cm pot and was taken 17 weeks after rooted cuttings were planted. Height measurements were taken from the soil line of the container. The test plants were grown under normal greenhouse conditions including 60–65° F. night temperatures and color readings were taken under natural greenhouse light. Color references are primarily to The R.H.S. Colour Chart of The Royal Horticultural Society of London except where general terms of ordinary dictionary significance were used.

The plant:

*Classification.*—Botanical — *Euphorbia pulcherrima*. Commercial — Festival Rose.

*Rooting habit.*—Abundant, thick, fibrous roots.

*Time to root.*—14 days in summer at 21° C., 18 days in winter at 21° C. using a stem tip cutting 5–6 cm long.

*Form.*—Upright when apical meristem is removed (pinching) leaving five or more nodes above the soil line. Generally all lateral shoots will emerge and develop with the lower shoots emerging first and growing longest, resulting in a canopy of bracts over the upper two-thirds of the plant.

*Habit and form of growth.*—Stong thick stems with excellent branch angles that hold up the large bracts and reduce lateral branch breakage during shipping. Growth is vigorous but with proper growing schedules, it can be grown with no or little growth regulators.

*Height.*—30 to 33 cm.

*Width.*—45 to 50 cm.

Foliage: Leaves are alternate and borne on 4.5 to 5 cm petioles with a reddish purple cast. Last 3 to 4 leaves before true bract also turn the same rose color.

*Size.*—Mature leaves are on average 11 to 12 cm long and 9 to 10 cm wide at broadest point near the basal area of the leaf. Leaves can vary greatly depending on the location of the plant.

*Shape.*—More lanceolate than ovate with acuminate apex and more truncate than rounded base.

*Texture.*—Upper — glabrous; Lower — glabrous and rugose because of protruding veins.

*Margin.*—Entire with slight lobing on some leaves.

*Color.*—Young Foliage — Top side, Yellow-Green Group 146A. Under side, Yellow-Green Group 146B. Mature Foliage — Top side, Yellow-Green Group 147A. Under side, Green Group 137B. Leaf Petiole — Greyed-Purple Group 187B, having an average width of 3 mm.

*Veins.*—Pinnate, Yellow-Green Group 146B on leaf underside.

Branching:

*Branch color.*—Yellow-Green Group 146A with a Red-Purple Group 60B cast.

*Internode length.*—25 mm.

*Lateral stem length.*—18 to 25 cm, basal is longest.

Flower:

*Flowering habits.*—Early flowering cultivar. Apparently having a longer critical day-length for development of flower initiation. Under controlled day-length, development time is approximately 8 weeks, but temperatures above 70° F. will cause more rapid development without heat delay. The cyathia area of the bract is 3 to 3.5 cm in diameter and 18 mm deep.

*Natural flowering season.*—November 17 to 20 under Lompoc, Calif. conditions.

*Flower time.*—8 weeks under 11 hours of day-length at 20° C. Does not heat delay at night temperatures above 23° C. Heat delay defined as the delay of flower bud initiation under short day conditions (about 10 hour day) at high night temperatures.

Cyathia:

*Description.*—In a tight cluster at the center of the bract and usually between 10 and 15 in number. Cyathia are stress tolerant, remaining in the involucre for a considerable time under low fertility, low light and high temperature conditions, even after the pollen is shed. Severe drying may cause cyathia to drop. Severe drying may cause them to drop.

*Color.*—Yellow-Green Group 144A with reddish tip, Yellow-Green Group 146C with Red Group 43A tip at maturity.

*Borne.*—Prominent on short stalks staying tightly clustered without growing apart (splitting). Usually 3 to 3.5 cm in diameter.

*Quantity.*—Highly dependent on cultural conditions with 10 to 15 cyathia per bract on a pinched plant.

*Size.*—Average length of 14 mm, average width of 6 mm.

Peduncles:

*Length.*—5 mm.

*Aspect.*—Upright to 45° angle depending on location.

*Color.*—Yellow-Green Group 146C.

Bracts:

*Primary.*—Shape — Ovate. Length — 14 cm. Width — 9 cm. Margin — Slightly lobed.

*Secondary.*—Shape — Oblong. Length — 6 cm. Width — 3.5 cm. Margin — Entire.

*Color.*—Maturity — Red Group 53C. Young bract — Red Group 53C. Under side — Red Group 53C.

*Bract aspect.*—Flat to slightly upright.

*Spread.*—25 to 30 cm.

*Number.*—20 to 25 bracts per plant with usually 5 inflorescences per plant, but can vary depending on conditions. Bract diameter also varies depending on conditions, pinched or non-pinched and if growth regulators are applied.

Reproductive organs:

*Stamens.*—Number — Numerous. Anther Shape — Oblong, having an average length of 4 mm. Color — Red-Purple Group 59B. Filament Color — Red-Purple Group 59B. Pollen — Abundant, yellow.

*Pistils.*—Stigma Shape — Forked. Color — Red-Purple Group 59B. Style Color — Red-Purple Group 59B. Ovaries: Number — 3 when stigma is receptive. Size — 3 mm. Color — Green-Yellow Group 144B.

*Nectar cups.*—Usually 1 per cyathia, but occasionally 2, Yellow-Orange Group 15A.

Post production longevity: 30 days or longer.

Presence of fruit/seeds: No seeds on plants as need to be hand pollinated to get seed set.

One seed set per female flower: Many seeds are only male.

Disease resistance: Bracts have shown resistance to botrytis and bract edge burn. No powdery mildew has been observed on leaves and bracts.

I claim:

1. A new and distinct variety of poinsettia plant as herein shown and described, particularly characterized by its unique rose color and bract shape; resistance to bract fading; long lasting cultivar and strong branch angles which reduce breakage of lateral branches during shipping.

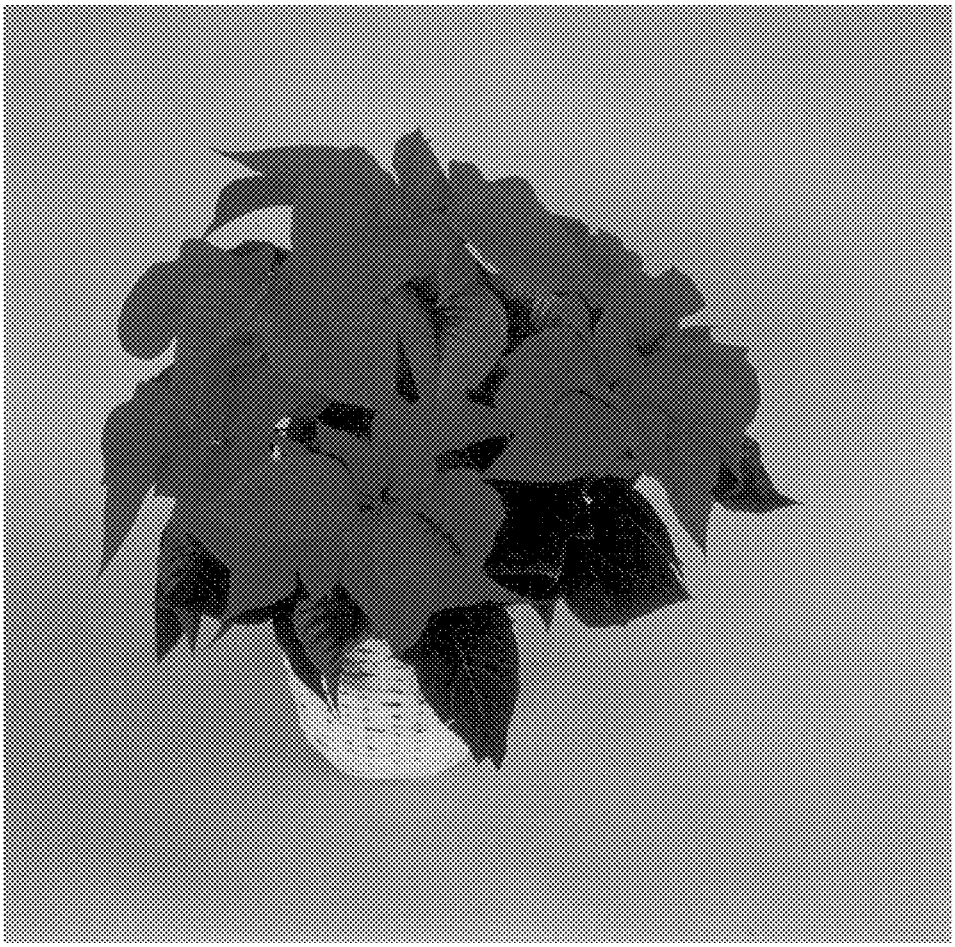

* * * * *